United States Patent [19]

Albright et al.

[11] 4,182,776

[45] Jan. 8, 1980

[54] METHOD OF TREATING LIPIDEMIA WITH ARYLOXYALKYLAMINOBENZOIC ACIDS AND ESTERS

[75] Inventors: Jay D. Albright, Nanuet; Thomas G. Miner, Chester; Robert G. Shepherd, South Nyack, all of N.Y.

[73] Assignee: American Cyanamid Company, Stamford, Conn.

[21] Appl. No.: 891,654

[22] Filed: Mar. 30, 1978

Related U.S. Application Data

[60] Division of Ser. No. 760,600, Jan. 19, 1977, abandoned, which is a continuation-in-part of Ser. No. 639,018, Dec. 9, 1975, abandoned.

[51] Int. Cl.$^2$ .................. A61K 31/445; A61K 31/38; A61K 31/34; C07C 101/60
[52] U.S. Cl. ..................................... 424/319; 424/267; 424/275; 424/285; 424/304; 424/308; 560/45; 560/47; 560/49; 560/50
[58] Field of Search ............... 424/267, 275, 285, 304, 424/308, 319; 560/45, 47, 49, 50

[56] References Cited

U.S. PATENT DOCUMENTS

| | | | |
|---|---|---|---|
| 2,946,799 | 7/1960 | Renz | 560/45 X |
| 3,551,478 | 12/1970 | Schmitt | 560/45 |
| 3,716,644 | 2/1973 | Albers | 424/308 |
| 3,784,697 | 1/1974 | Nahm | 424/319 |
| 3,868,416 | 2/1975 | Albright | 424/319 |
| 3,924,001 | 12/1975 | Albright | 424/319 |

FOREIGN PATENT DOCUMENTS 51-101939  9/1976  Japan ....................... 424/319

*Primary Examiner*—Anna P. Fagelson
*Attorney, Agent, or Firm*—Edward A. Conroy, Jr.

[57] ABSTRACT

Aryloxyalkylaminobenzoic acids and esters as hypolipemic compounds.

10 Claims, No Drawings

METHOD OF TREATING LIPIDEMIA WITH ARYLOXYALKYLAMINOBENZOIC ACIDS AND ESTERS

CROSS-REFERENCE TO RELATED APPLICATION

This application is a division of our copending application Ser. No. 760,600, filed Jan. 19, 1977, which in turn is a continuation-in-part of our application Ser. No. 639,018, filed Dec. 9, 1975, both now abandoned.

BACKGROUND OF THE INVENTION

No hypolipemic activity has been reported in the literature for the compounds of the instant invention; however, the ethyl ester of p-(2-phenoxyethylamino)-benzoic acid is disclosed in Chem. Abstracts, 54, p 24808C.

SUMMARY OF THE INVENTION

This invention relates to novel aryloxyalkylaminobenzoic acids and esters. They are useful as synthetic hypolipidemic compounds for the treatment of artherosclerosis by virtue of their lowering cholesterol, triglycerides, and phospholipids in serum. The compounds of the instant invention can be used to lower serum lipids without interfering at a late stage of the biosynthesis of cholesterol. They are novel in chemical type and possibly in mode of action.

DESCRIPTION OF THE INVENTION

This invention is concerned with compounds of the following formula:

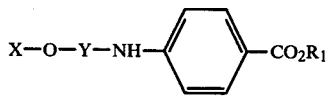

wherein Y is a branched or straight alkyl chain $C_nH_{2n}$ wherein n is 2 to 12 for method of treatment claims and n is 2 to 12 for new product claims with the proviso that when n=2 then X must not be unsubstituted-phenyl; $R_1$ is selected from the group consisting of hydrogen, loweralkyl, phenyl, p-chlorophenyl, benzyl, diloweralkylaminoethyl, loweralkoxyethyl, loweralkylaminoethyl, diloweralkylaminopropyl, 3-loweralkoxy-2-hydroxypropyl, 2,3-dihydroxypropyl, 3-loweralkylamino-2-hydroxypropyl, 3-diloweralkylamino-2-hydroxypropyl, 3-amino-2-hydroxypropyl, 2-loweralkanoylaminoethyl, 3-loweralkanoylaminopropyl 3-loweralkanoyloxy-2-hydroxypropyl, 3-loweralkanoyloxy-2-loweralkanoyloxypropyl, 3-loweralkanoylamino-2-hydroxypropyl, 3-loweralkanoylamino-2-loweralkanoyloxypropyl, 1-methyl-4-piperidyl, 2-pyridylmethyl, 3-pyridylmethyl, and 4-pyridylmethyl; and X is selected from the group consisting of phenyl, naphthyl, thienyl, furyl, 1,2,3,4-tetrahydronaphthyl, 4-chloro-1-naphthyl, and substituted phenyl, wherein the phenyl substituents are halogen, hydroxyl, loweralkoxy, loweralkyl, cyano, trihalomethyl, amino, loweralkanoylamino, loweralkylamino, diloweralkylamino, phenoxy, p-chlorophenoxy, benzyloxy, p-chlorobenzyloxy and cycloalkyl; and when $R_1$ is hydrogen, the alkali metal or organic base salts thereof.

Suitable loweralkyl groups contemplated by this invention are those having 1 to 6 carbon atoms, as for example, methyl, ethyl, isopropyl, propyl, tert-amyl, n-hexyl and tert-butyl.

Suitable $C_nH_{2n}$ alkyl chains are both branched and straight-chain alkyls wherein the branched chain is a lower-alkyl group of 1 to 6 carbon atoms.

This invention is also concerned with a method of lowering the sterol and triglyceride level of the serum of warm-blooded animals, employing pharmaceutical dosage forms of the compounds of the formulae

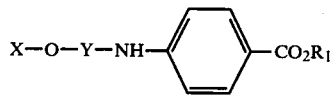

wherein X, Y and $R_1$ are as previously defined, as well as the pharmaceutically acceptable acid-addition salts—and where $R_1$ is hydrogen, the alkali metal or organic base carboxylic acid salts thereof.

The novel compounds of the present invention are colorless or tan crystalline solids or colorless or tan oils. The compounds are in general soluble in organic solvents such as benzene, chloroform, dichloromethane, N,N-dimethylformamide, dimethyl sulfoxide and lower alkanols.

The compounds of the present invention are bases and may be converted to their non-toxic addition salts with acids such as sulfuric, hydrochloric, phosphoric, succinic, citric, and the like. The compounds wherein $R_1$ is hydrogen may be reacted with bases such as sodium hydroxide, potassium hydroxide and the like or with organic bases such as ammonium hydroxide, pyridine, mono, di or tri loweralkylamines such as methylamine, diethylamine, trimethylamine, dibutylamine, and the like to obtain the corresponding carboxylic acid salts.

The novel compounds are prepared by reacting loweralkyl p-aminobenzoates, p-aminobenzoic acid or other esters of p-aminobenzoic acid with alkylating agents such as aryloxyalkylhalides, aryloxyalkanol O-sulfates, O-tosylates, O-trifluoromethanesulfonates, or O-methanesulfonates with or without a solvent at 50° to 150° C. for 1–25 hours.

Suitable solvents for the alkylations are hexamethylphosphoramide, N,N-dimethylformamide, N,N-dimethylacetamide, lower alkanols, chloroform, dimethyl sulfoxide, benzene, xylene, acetonitrile and the like.

The alkylation reactions may be carried out with an equivalent of base such as an alkali carbonate or bicarbonate. Alternatively, the p-(aryloxyalkyl)aminobenzoates may be prepared by reaction of loweralkyl p-aminobenzoates with an aryloxyalkylhalide in the presence of an equivalent of sodium hydroxide in inert solvents such as hexamethylphosphoramide, N,N-dimethylformamide, N,N-dimethylacetamide, xylene and the like at 50° to 170° C. for 1–25 hours.

In the case of aryloxyalkylchlorides, the alkylations of loweralkyl p-aminobenzoates may be carried out with an equivalent of sodium or potassium iodide in inert solvents such as hexamethylphosphoramide, N,N-dimethylformamide, N,N-dimethylacetamide and the like.

The p-(aryloxyalkyl)aminobenzoic acids of this invention are prepared by hydrolysis of the corresponding esters by reacting with alkali metal hydroxides such as sodium hydroxide or potassium hydroxide in a lower alkanol, water, or an aqueous lower alkanol at 25° to 100° C. Alternatively, the p-(aryloxyalkyl)aminobenzoic acids may be prepared by hydrolysis of the p-(aryloxyalkyl)aminobenzoates with mineral acids such as hydrochloric, hydrobromic or sulfuric in water or aqueous alkanols.

Esters of p-(aryloxyalkyl)aminobenzoic acids may be prepared by conversion of the appropriate acids to an acid chloride with reagents such as thionyl chloride and oxalyl chloride and reacting the intermediate acid chlorides with lower alkanols, diloweralkylaminoethanols, lower alkoxyethanols and the like. Alternatively, the metal (sodium, potassium, Zinc and the like) carboxylic acid salts may be reacted with lower alkylhalides, and substituted propylhalides such as 3-halo-1,2-propanediol and the like in solvents such as hexamethylphosphoramide or N,N-dimethylformamide, to give esters of p-(aryloxyalkyl)aminobenzoic acids of formulae I.

The novel p-(aryloxyalkyl)aminobenzoates of the present invention may be prepared by reductive alkylation of a loweralkyl p-aminobenzoate or p-aminobenzoic acid with a suitable aryloxyalkylaldehyde or ketone in the presence of noble metal and (or) nickel or cobalt catalyst or a suitable metal hydride. For example Raney nickel, hydrogen and an aryloxyalkylaldehyde may be used to reductively alkylate ethyl p-aminobenzoate. Auxiliary catalysts such as aluminum chloride, piperidine acetate, or acids may be used in the reductive alkylation.

Some of the alkylating agents for the preparation of the novel compounds of this invention may be prepared in the following manner: where W=halogen; n=0, 1-11; $R_1$ is hydrogen or loweralkyl; $R_1$ and $R_2$ are hydrogen or lower alkyl.

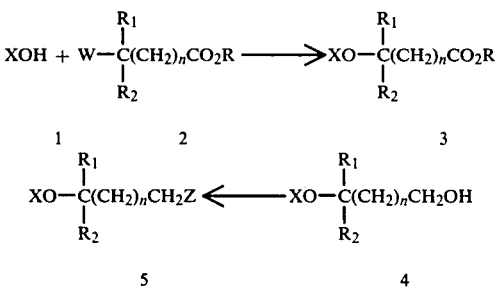

Reduction of the intermediate aryloxyalkyl derivatives 3 gives the corresponding alcohols 4 which are converted to the desired alkylating reagents 5 (where Z is halogen, O-methanesulfonate and the like).

The compounds of the present invention show hypolipidemic activity. The mechanism of action of these compounds is not known and the inventors do not wish to be limited to any particular mechanism. However, the compounds of the present invention were shown to possess hypolipidemic activity as determined by animal experiments as follows: The compounds were administered orally admixed with the diet to groups of 4 to 6 male rats, CFE strain from Carworth Farms. A control group of 6 to 8 rats was maintained on the diet alone; test groups were maintained on the diet plus the indicated percentage of compound by weight. After 6 days treatment serum sterol concentrations were determined by the extraction method of H. H. Leffler, Amer. J. Clin. Path. 31, 310 (1959), the overall method appropriately modified for use with an automatic mechanical analyzer and the colorimetric determination of Zlatkis et al., J. Lab. Clin. Med. 44, 486 (1953). Serum triglycerides were estimated by the automated procedure of Kessler and Lederer ["Automation in Analytical Chemistry", Skeggs, L. T., (Ed.), Mediad, Inc., New York, 1965, p. 341]. In these tests a compound is considered to have hypolipidemic activity if it depresses serum sterol levels below that of the controls, and/or depresses triglyceride levels below controls. Table I shows several of the compounds of the present invention and the degree to which they depress serum sterols and triglyceride levels after a one week dosing period.

TABLE I

| Compound | % Compound In Diet | % Lowering of Serum Levels | |
|---|---|---|---|
| | | Sterol | Triglyceride |
| p-[(2-Phenoxyethyl)amino]benzoic Acid | 0.1 | 22 | 41 |
| Ethyl p-[(2-phenoxyethyl)amino]benzoate | 0.1 | 21 | 41 |
| p-[(3-Phenoxypropyl)amino ]benzoic Acid | 0.1 | 16 | 31 |
| Ethyl p-[(3-phenoxypropyl)amino]benzoate | 0.1 | 10 | 27 |
| p-[(4-Phenoxybutyl)amino]benzoic Acid | 0.1 | 4 | 53 |
| Ethyl p-[(6-phenoxyhexyl)amino]benzoate | 0.05 | 19 | 15 |
| p-{[2-(p-Bromophenoxy)ethyl]amino}benzoic Acid | 0.1 | 10 | 47 |
| p-[(11-Phenoxyundecyl)amino]benzoic Acid | 0.1 | 7 | 41 |
| p-{[2-(2-Naphthyloxy)ethyl]amino}benzoic Acid | 0.1 | 13 | 47 |
| Ethyl p-{[2-(2-naphthyloxy)ethyl]amino}benzoate | 0.1 | 10 | 43 |
| p-[(2-Phenoxypropyl)amino]benzoic Acid | 0.05 | 24 | 52 |
| p-{[2-(1-Naphthyloxy)ethyl]amino}benzoic Acid | 0.1 | 17 | 42 |
| p-2-(p-Fluorophenoxy)propylamino benzoic Acid | 0.1 | 44 | 64 |
| Ethyl p-2-(4-Fluorophenoxy)propylamino benzoate | 0.1 | 30 | 74 |

The compounds of the present invention are useful as hypolipidemic agents in mammals when administered in amounts ranging from about 0.5 mg per kg to about 40 mg per kg of body weight per day. A preferred dosage regimen for optimum results would be from about 2 mg per kg to about 29 mg per kg of body weight per day. Thus the daily dosage employed for a subject of about 70 kg is about 35 mg to about 2.8 g and preferably about 140 mg to about 2.0 g.

The active compounds of the present invention may be orally administered, for example, with an inert diluent or with an assimilable edible carrier, or they may be enclosed in hard or soft gelatin capsules, or they may be compressed into tablets, or they may be incorporated directly with the food of the diet. For oral therapeutic administration the active compounds of this invention may be incorporated with excipients and used in the form of tablets, troches, capsules, elixirs, suspensions, syrups, wafers, chewing gum or the like. Such compositions and preparations should contain at least 0.1% of active compound. The percentage in the compositions and preparations may, of course, be varied and may conveniently be between about 5% and 75% or more of the weight of the unit. The amount of active compound in such therapeutically useful compositions or preparations is such that a suitable dosage will be obtained. Preferred compositions or preparations are prepared so that an oral dosage unit form contains between about 10 mg and 500 mg of active compound.

The tablets, troches, pills, capsules and the like may also contain the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; and a sweetening agent such as sucrose, lactose or saccharin may be added or a flavoring. When the dosage unit form is a capsule, it may contain in addition to materials of the above type a liquid carrier such as a fatty oil. Various other materials may be present as coatings or to otherwise modify the physical form of the dosage unit. For instance, tablets, pills or capsules may be coated with shellac, sugar or both. A syrup or elixir may contain the active compounds, sucrose as a sweetening agent, methyl and propyl parabens as preservatives, a dye and a flavoring such as cherry or orange flavor. Any material used in preparing any dosage unit form should be pharmaceutically pure and substantially non-toxic in the amounts employed.

In addition, the active ingredients may be incorporated into sustained release preparations.

SPECIFIC DISCLOSURE

EXAMPLE 1

6-(2-Naphthyloxy)-1-hexanol

To a chilled round bottom flask is added, 4.2 g of 57% sodium hydride in oil, 50 ml of hexamethylphosphoramide and 15.8 g. of 2-naphthol. After ½ hour the mixture is allowed to warm to room temperature and 13.6 g. of 6-chlorohexan-1-ol is added. The mixture is heated at 110° C. overnight, cooled, diluted with water and extracted with ether. The ether extract is washed with sodium hydroxide solution, then with water, dried (magnesium sulfate) and the solvent removed under vacuum. The solid is dissolved in ether and the solution washed with sodium hydroxide solution. The ether layer is dried (magnesium sulfate) and the solvent removed under vacuum to give 15.9 g. of product, as crystals, mp 53°–56° C.

EXAMPLE 2

6-(2-Naphthyloxy)-1-hexanol O-methanesulfonate

To a mixture of 10.4 g. of 6-(2-naphthyloxy)-1-hexanol and 8.1 g. of triethylamine in 250 ml. of dichloromethane chilled to −8° C. under nitrogen is added dropwise 5.1 g of methanesulfonyl chloride. After one hour at 0° to −8° C., the mixture is washed with cold water, 10% hydrochloric acid solution, saturated sodium bicarbonate solution, saturated sodium chloride solution, and dried (magnesium sulfate). The solvent is removed under vacuum to give the product as a white solid.

EXAMPLE 3

Ethyl p-{[6-(2-naphthyloxy)hexyl]amino}benzoate

A solution of 10.0 g of 6-(2-naphthyloxy)-1-hexanol O-methanesulfonate and 9.7 g of ethyl 4-aminobenzoate in 50 ml of hexamethylphosphoramide is heated at 110° C. for 16 hours. The solution is cooled, diluted with water, filtered and the solid washed with ethanol and water to give 7.7 g of product. Recrystallization from ethanol and once from acetone-hexane gives crystals, mp 109°–110° C.

EXAMPLE 4 p-{[6-(2-Naphthyloxy)hexyl]amino}benzoic acid

A solution of 4.8 g of ethyl p-{[6-(2-naphthyloxy)hexyl]amino}benzoate and 4.8 g of potassium hydroxide in 100 ml of 95% ethanol is refluxed for 3 hours. The solution is cooled, diluted with water and acidified with concentrated hydrochloric acid. The mixture is filtered and the solid washed with ethanol with water and recrystallized from ether-methylene chloride and acetone to give crystals, mp 157°–159° C.

EXAMPLE 5

2-(2-Naphthyloxy)ethanol

A solution of 14.4 g of 2-naphthol, 12.1 g of 2-bromoethanol and 5.9 g of sodium methoxide in 100 ml of ethanol is allowed to stand two days at room temperature. The solvent is removed under vacuum and the residue extracted with ether. The ether extract is washed with water dried (magnesium sulfate) and the solvent removed under vacuum to give crystals, mp 65°–70° C.

EXAMPLE 6

2-(2-Naphthyloxy)ethanol O-methanesulfonate

As described in Example 2, 13.5 g of 2-(2-naphthyloxy)ethanol in 400 ml of dichloromethane is reacted with 9.5 g of methanesulfonyl chloride in the presence of 11.4 g of triethylamine to give the product as tan crystals.

EXAMPLE 7

Ethyl p-{[2-(2-naphthyloxy)ethyl]amino}benzoate

A mixture of 18.7 g of 2-(2-naphthyloxy)ethanol O-methanesulfonate and 23.6 g of ethyl p-aminobenzoate is heated in 300 ml of hexamethylphosphoramide at 110° C. for 16 hours. The mixture is cooled, diluted with water, and worked up as described in Example 3 to give the crystalline product. Recrystallization from ethanol gives crystals, mp 158°–162° C.

EXAMPLE 8

2-(2-Thienyl)ethanol O-methanesulfonate

A mixture of 12.8 g of 2-(2-thienyl)ethanol and 20.2 g of triethylamine in 500 ml of dichloromethane is reacted with 12.6 g of methanesulfonyl chloride as described in Example 2 to give the product as an oil.

EXAMPLE 9

Ethyl p-[2-(2-thienyl)ethylamino]benzoate

A mixture of 33.0 g of ethyl p-aminobenzoate and 2-(2-thienyl)ethanol o-methanesulfonate in 100 ml of hexamethylphosphoramide is heated at 125° C. for 16 hours. The solution is cooled, diluted with water and extracted with ether. The ether extracts are dried (magnesium sulfate) and the solvent removed under vacuum. The residual oil is chromatographed over silica gel (chloroform). The solvent is removed from the fractions containing the product giving crystals. Recrystallization from hexane gives crystals. mp 93°–96° C.

EXAMPLE 10 p-[2-(2-Thienyl)ethylamino]benzoic acid

A mixture of 29.7 g of ethyl p-[2-(2-thienyl)ethylamino]benzoate and 29 g of potassium hydroxide in 200 ml of 95% ethanol is refluxed for 3 hours. The mixture is worked up as described in Example 4 to give the product, mp 161°-163° C.

EXAMPLE 11

2-(1-Naphthyloxy)ethanol O-methanesulfonate

To a solution of 18.8 g of 2-(1-naphthyloxy)ethanol and 15.1 g of triethylamine in 425 ml of dichloromethane is added 12.6 g of methanesulfonyl chloride as described in Example 1 to give the product.

EXAMPLE 12

Ethyl p-{[2-(1-Naphthyloxy)ethyl]amino}benzoate

A solution of 29.1 g of 2-(1-naphthyloxy)ethanol O-methanesulfonate and 33 g of ethyl p-aminobenzoate in 100 ml of hexamethylphosphoramide is heated at 100° C. for 16 hours. The solution is worked up as described in Example 3 to give the product. Recrystallization gives crystals, mp 124°-127° C.

EXAMPLE 13 p-{[2-(1-Naphthyloxy)ethyl]amino}benzoic acid

A solution of 12 g of ethyl p-[2-(1-naphthyloxy)ethylamino]benzoate and 15.8 g of potassium hydroxide in 100 ml of 95% ethanol is refluxed for 3 hours. The solution is diluted with 75 ml of water and acidified with concentrated hydrochloric acid. The solid is filtered, washed with 50% ethanol and with water. Recrystallization from ethanol gives the product as crystals, mp 193°-194° C.

EXAMPLE 14

Ethyl p-{[2-(2,4-dichlorophenoxy)ethyl]amino}benzoate

A solution of 22.8 g of β-bromo-2,4-dichlorophenetole and 29.8 g of ethyl 4-aminobenzoate in 100 ml of hexamethylphosphoramide is heated at 125° C. for 16 hours. The solution is chilled, diluted with water (80 ml) and filtered. The solid is washed with 50% ethanol to give the product. Recrystallization from ethanol gives crystals, mp 111°-113° C.

EXAMPLE 15 p-{[2-(2,4-Dichlorophenoxy)ethyl]amino}benzoic acid

A solution of 15 g of ethyl p-{[2-(2,4-dichlorophenoxy)ethyl]amino}benzoate and 15 g of potassium hydroxide in 200 ml. of 95% ethanol is refluxed for 3 hours. The solution is cooled, diluted with water, acidified with concentrated hydrochloric acid and filtered. The solid is recrystallized from ethanol to give crystals, mp 203°-205° C.

EXAMPLE 16

6-(Phenoxy)-1-hexanol

To a solution of 10.3 g of phenol in 25 ml of hexamethylphosphoramide is added 4.2 g of 57% sodium hydride in oil. After hydrogen evolution ceases, 13.6 g of 6-chlorohexan-1-ol in 25 ml of hexamethylphosphoramide is added and the mixture heated at 110° C. for 16 hours. The solution is cooled, diluted with water and extracted with ether. The ether extracts are washed with sodium hydroxide solution, dried (magnesium sulfate) and the solvent removed under vacuum to give white crystals, mp 69°-74° C.

EXAMPLE 17

6-(Phenoxy)-1-hexanol O-methanesulfonate

To a chilled (−2° C.) mixture of 9.7 g of 6-(phenoxy)-1-hexanol in 250 ml of dichloromethane containing 11.1 g of triethylamine is added 6.95 g of methanesulfonyl chloride. The product is isolated as described in Example 2 to give the product as an oil.

EXAMPLE 18

Ethyl p-(6-phenoxyhexylamino)benzoate

A solution of 13.6 g of 6-(phenoxy)-1-hexanol O-methanesulfonate and 16.5 g of ethyl p-aminobenzoate in 75 ml of hexamethylphosphoramide is heated at 110° C. for 16 hours. The product is isolated as described in Example 3 to give crystals. Recrystallization from ethanol gives crystals, mp 105°-108° C.

EXAMPLE 19 p-(6-Phenoxyhexylamino)benzoic acid

A mixture of 5 g of ethyl p-[6-(phenoxyhexyl)amino]benzoate and 5 g of potassium hydroxide in 100 ml of 95% ethanol is refluxed for 3 hours. The mixture is cooled, acidified with concentrated hydrochloric acid, diluted with water and filtered. The solid is washed with water and 50% ethanol to give crystals, mp 168°-170° C.

EXAMPLE 20

11-Phenoxyundecanoic acid

To a mixture of 9.4 g of phenol, 26.5 g of 11-bromoundecanoic acid and 250 ml of hexamethylphosphoramide chilled in an ice bath is added 10.5 g of sodium methoxide. A viscous mass developes and the mixture is stirred and heated at 100° C. for 20 hours. The mixture is diluted with cold water, acidified with concentrated hydrochloric acid, filtered and the solid washed with water to give gray crystals. Recrystallization from acetone gives pale gray crystals, mp 76°-78° C. A second crop of crystals is obtained from mother liquors, mp 75°-77° C.

EXAMPLE 21

11-Phenoxy-1-undecanol

To 100 ml of 1M diborane in tetrahydrofuran under nitrogen chilled in an ice bath is added dropwise 13.92 g of 11-phenoxyundecanoic acid in 50 ml of tetrahydrofuran over 30 minutes. The solution is allowed to stand at room temperature for 19 hours and is poured onto ice. After standing, the mixture is filtered and the solid washed with water to give white crystals, mp 56°-58° C. A sample on recrystallization from ethanol gives white crystals, mp 56.5°-57.5° C.

EXAMPLE 22

11-Phenoxy-1-undecanol O-methanesulfonate

To a solution of 10.6 g of 11-phenoxy-1-undecanol, 200 ml of dichloromethane and 8.4 ml of triethylamine chilled to −8° C. in an ice-salt bath is added dropwise over 10 minutes, a solution of 3.38 ml of methanesulfonyl chloride in 10 ml of dichloromethane. The solution is stirred for 30 minutes at −8° C., washed with 150 ml of ice-cold water, 75 ml of cold 10% hydrochloric acid, 75 ml of cold saturated sodium bicarbonate, 75 ml of cold saturated sodium chloride solution and dried over magnesium sulfate. The solvent is removed in vacuo to give off-white crystals, mp 54°–58° C.

EXAMPLE 23

Ethyl p-[(11-phenoxyundecyl)amino]benzoate

A mixture of 16.5 g of ethyl p-aminobenzoate, 10.3 g of 11-phenoxy-1-undecanol O-methanesulfonate and 50 ml of hexamethylphosphoramide is heated at 100°–110° C. for 20 hours, chilled, and diluted with 30 ml of ethanol and 10 ml of water. Chilling and filtering gives a solid which is washed with ethanol-water (1:1) and with water to give yellow crystals, mp 83°–87° C. Recrystallization from ethanol gives yellow needles, mp 89°–90° C.

EXAMPLE 24 p-(4-Phenoxybutylamino)benzoic acid

To a mixture of 15 ml of hexamethylphosphoramide, 0.86 g of sodium hydride (56% in oil) and 4.32 g of 1,4-dibromobutane chilled in an ice bath is added dropwise, over ¾ hour, 1.88 g of phenol in 15 ml of hexamethylphosphoramide. The mixture is stirred at 0° C. for one hour, 3.30 g of ethyl p-aminobenzoate is added and the mixture is heated on a steam bath for 16 hours. The mixture is chilled, diluted with 15 ml of water, chilled, filtered and the solid washed with ethanol-water (1:1) to give tan crystals.

To 4.7 g of crude product is added 5 g of potassium hydroxide and 80 ml of ethanol-water (9:1) and the mixture is refluxed for 3 hours. While hot, the mixture is acidified with concentrated hydrochloric acid and diluted with water. Chilling and filtering gives tan crystals. This crude product is dissolved in chloroform and filtered through silica gel. After washing with chloroform, the product is removed by washing with benzene-acetic acid (3:1) and chloroform-acetic acid (3:1). The solvent is removed and the product recrystallized from ethanol to give tan crystals, mp 153°–155° C.

EXAMPLE 25

Ethyl p-{[2-(p-bromophenoxy)ethyl]amino}benzoate

A mixture of 26.4 g of ethyl p-aminobenzoate, 22.4 g of 2-bromoethyl p-bromophenyl ether and 80 ml of hexamethylphosphoramide is heated at 100°–110° C. for 20 hours. The mixture is chilled, diluted with 25 ml of water, chilled and filtered. The solid is washed with 100 ml of ethanol-water (1:1), with 25 ml of ethanol and with water to give tan crystals, mp 128°–133° C. Recrystallization from ethanol gives yellow crystals, mp 135.5°–137° C.

EXAMPLE 26 p-{[2-(p-Bromophenoxy)ethyl]amino}benzoic acid

A mixture of 10.0 g of ethyl p-{[2-(p-bromophenoxy)ethyl]amino}benzoate, 10 g of potassium hydroxide and 100 ml of ethanol-water (9:1) is refluxed for 3.5 hours. The mixture is acidified while hot with concentrated hydrochloric acid, diluted with water, chilled and filtered. The solid is washed with water to give crystals, mp 190°–192° C. Recrystallization from ethanol (500 ml) gives white crystals, mp 194°–196° C.

EXAMPLE 27 p-[(11-Phenoxyundecyl)amino]benzoic acid

A mixture of 7.0 g of ethyl p-[(11-phenoxyundecyl)amino]benzoate, 7.0 g of potassium hydroxide and 150 ml of ethanol-water (9:1) is refluxed for 3.5 hours. The mixture is made acidic while hot with concentrated hydrochloric acid, diluted with water, cooled and filtered to give white crystals, mp 117°–119° C. Recrystallization from ethanol gives white crystals, mp 118°–119.5° C.

EXAMPLE 28

Ethyl p-[2-phenoxyethylamino)benzoate

A mixture of 33 g of ethyl p-aminobenzoate, 80 ml of hexamethylphosphoramide and 20.1 g of β-bromophenetole is heated at 110° C. for 20 hours. The mixture is cooled, diluted with 25 ml of water, chilled, filtered and the solid washed with ethanol and with water to give crystals, mp 126°–129° C. Recrystallization from ethanol gives pale yellow crystals, mp 129°–131° C.

EXAMPLE 29 p-(2-Phenoxyethylamino)benzoic acid

A mixture of 12 g of ethyl p-(2-phenoxyethylamino)benzoate, 12 g of potassium hydroxide and 200 ml of ethanol-water (9:1) is refluxed for 3.5 hours. The solution is acidified while hot with concentrated hydrochloric acid, diluted with water, cooled, filtered and the solid washed with water to give crystals, mp 172°–175° C. Recrystallization from ethanol gives off-white crystals, mp 174°–176° C.

EXAMPLE 30

Ethyl p-[(3-phenoxypropyl)amino]benzoate

A mixture of 33 g of ethyl p-aminobenzoate, 21.5 g of 3-bromopropylphenyl ether and 100 ml of hexamethylphosphoramide is heated at 100°–110° C. in an oil bath for 20 hours. The mixture is chilled, diluted with 50 ml of water, chilled and filtered. The solid is washed with ethanol-water (1:1) and with water to give yellow crystals, mp 73°–74° C.

EXAMPLE 31 p-[(3-Phenoxypropyl)amino]benzoic acid

A mixture of 15 g of ethyl p-[(3-phenoxypropyl)amino]benzoate, 15 g of potassium hydroxide and 150 ml of ethanol-water (9:1) is refluxed for 3.5 hours. The mixture is acidified while hot with concentrated hydrochloric acid, diluted with water, chilled and filtered to give yellow crystals, mp 159°–162° C. Recrystallization from ethanol gives pale yellow crystals, mp 161°–163° C.

EXAMPLE 32

2-Phenoxy-1-propanol

To 200 ml of one molar borohydride in tetrahydrofuran chilled in an ice bath under nitrogen is added dropwise with stirring 24.9 g of 2-phenoxypropionic acid in 100 ml of dry tetrahydrofuran over 25 minutes. The mixture is allowed to stand at room temperature for 23 hours and is poured onto ice. After standing, the mixture is extracted with dichloromethane and the extracts dried (magnesium sulfate) and concentrated under vacuum to give the product as a yellow oil.

EXAMPLE 33

2-Phenoxy-1-propanol O-methanesulfonate

To a solution of 15.2 g of 2-phenoxy-1-propanol, 20.8 ml of triethylamine and 300 ml of dichloromethane chilled to −10° C. in an ice-salt bath, is added dropwise 7.78 ml of methanesulfonyl chloride over 10 minutes. The solution is stirred at −10° C. for 30 minutes, washed with 100 ml of ice water, 100 ml of cold 10% hydrochloric acid, 100 ml of cold saturated sodium bicarbonate solution, 100 ml of cold saturated sodium chloride solution and dried (magnesium sulfate). The solvent is removed under vacuum to give the product as an oil.

EXAMPLE 34 p-[(2-Phenoxypropyl)amino]benzoic acid

A mixture of 33 g of ethyl p-aminobenzoate, 0.10 mole of 2-phenoxy-1-propanol O-methanesulfonate and 80 ml of hexamethylphosphoramide is heated at 125° C. for 18 hours. The mixture is chilled, poured into water and extracted with ether. The ether extract is washed with water, dried over magnesium sulfate and concentrated under vacuum to an oil. The oil is combined with 250 ml of ethanol-water (9:1) and 20 g of potassium hydroxide and the mixture refluxed for 3.5 hours. The mixture is acidified with concentrated hydrochloric acid, diluted with water and extracted with chloroform. The chloroform extracts are washed with water, dried (magnesium sulfate) and concentrated under vacuum to give an oil. Ethanol is added and the mixture chilled and filtered to give the product, mp 140°–144° C. Recrystallization gives the product as crystals, mp 145°–147° C.

EXAMPLE 35

2-[p-(Benzyloxy)phenoxy]-2-methyl-propionic acid

To a solution of 10.0 g of hydroquinone monobenzyl ether in 40 ml of hexamethylphosphoramide is added 2.7 g of sodium methoxide. The mixture is stirred 10 minutes and 10.3 g of ethyl 2-bromoisobutyrate is added. The mixture is heated at 120° C. for 22 hours. After standing, the mixture is filtered. The solid is dissolved in 150 ml of ethanol-water (9:1) and 10 g of potassium hydroxide is added. The mixture is refluxed for 6 hours, acidified with concentrated hydrochloric acid, diluted with water, filtered and the solid washed with water to give crystals. The crystals ae dissolved in aqueous sodium hydroxide and the solution extracted once with chloroform and once with ether. The aqueous layer is acidified with concentrated hydrochloric acid and the mixture filtered. The solid is recrystallized from glacial acetic acid to give white crystals, mp 134°–137° C.

Reduction with borohydride-tetrahydrofuran gives 2-[p-(benzyloxy)phenoxy]propan-1-ol which is converted to the O-methanesulfonate and used as an alkylating agent.

EXAMPLE 36

Ethyl 2-[p-(benzyloxy)phenoxy]propionate

To 20.0 g of p-(benzyloxy)phenol in 80 ml of dry hexamethylphosphoramide is added 5.4 g of sodium methoxide. The mixture is stirred 10 minutes and 18.1 g of ethyl 2-bromopropionate is added (exotherm). After 15 minutes the mixture is heated on a steam bath for 16 hours. The mixture is poured onto ice, extracted with ether, the ether extracts washed with water, dried over magnesium sulfate and concentrated in vacuo to give off-white crystals, mp 36°–44° C. Two recrystallizations from ethanol give off-white crystals, mp 46°–49° C.

EXAMPLE 37 p-{[2-(2-Naphthyloxy)ethyl]amino}benzoic acid

A mixture of 3.0 g of ethyl p-{[2-(2-naphthyloxy)-ethyl]amino}benzoate, and 3.0 g of potassium hydroxide in 200 ml of ethanol-water (95:5) is refluxed for 3 hours. The mixture is diluted with 100 ml of water and brought to pH 6.0 with concentrated hydrochloric acid. The mixture is filtered and the solid washed with 50 ml of water and 20 ml of cold ethanol-water (4:1) to give the product, mp 208°–211° C.

EXAMPLE 38

Ethyl 4-{2-[4-(chlorophenoxy)propyl]amino}benzoate

A mixture of 15.1 g of ethyl p-aminobenzoate and 11.3 g of 2-(4-chlorophenoxy)-1-propanol O-methanesulfonate in 100 ml of hexamethylphosphoramide is heated at 115°–120° C. for 4.8 hours. The solution is cooled and partitioned between ether and water. The ether layer is separated and the aqueous layer extracted with ether. The combined ether extracts are dried (magnesium sulfate) and the solvent removed under reduced pressure to give 23 g. of semi solid. An 8 g. sample of the residue is chromatographed over silica gel with chloroform as eluent. The first fraction contains 3.8 g. of solid which is chromatographed on silica gel column with hexane-ethyl acetate and eluent. The first fraction gives 1.72 g. of tan solid. A sample (0.45 g.) is recrystallized from cyclohexane to give 0.3 g. of white needles, m.p. 96°–98° C.

EXAMPLE 39

Ethyl 4-{[3-(4-chlorophenoxy)propyl]amino}benzoate

A mixture of 17.1 g. of ethyl p-aminobenzoate, 14.6 g. of 3-(4-chlorophenoxy)-1-propanol O-methanesulfonate and 100 ml. of hexamethylphosphoramide is heated at 110°–115° C. for 16 hours. The solution is diluted with 100 ml. of water, allowed to cool and is filtered to give 12.5 g. of solid. Recrystallization from cyclohexane gives 7.8 g. of yellow needles. Chromatography over silica gel gives 6.8 g. of product as white crystals, m.p. 87°–88° C.

EXAMPLE 40

4-{[3-(4-chlorophenoxy)propyl]amino}benzoic Acid

A mixture of 4.5 g. of ethyl 4-{[3-(4-chlorophenoxy)-propyl]amino}benzoate 4.5 g. of potassium hydroxide and 100 ml. of 95% ethanol is refluxed for 3 hours. The solution is acidified with hydrochloric acid and the mixture is diluted with 100 ml. of water to give 3.7 g. of solid. Recrystallization by dissolving in a mixture of chloroform-ethyl acetate and diluting with hexane gives 3.3 g. of product as off-white crystals, m.p. 180°–181° C.

EXAMPLE 41

2-(4-chlorophenoxy)-1-propanol O-methanesulfonate

To a solution of 8.5 g. of 2-(4-chlorophenoxy)-1-propanol, 9.2 g. of triethylamine and 250 ml. of dichloromethane chilled to −5° C. are added dropwise 5.7 g of methanesulfonyl chloride. The solution is allowed to stand at room temperature for 1 hour and is washed with 100 ml portions of water, 10% hydrochloric acid, saturated sodium bicarbonate and saturated sodium chloride. The organic layer is dried (magnesium sulfate) and the solvent removed under vacuum to give 11.3 g of product as an oil.

EXAMPLE 42

3-(4-chlorophenoxy)-1-propanol O-methanesulfonate

To a solution of 9.7 g of 3-(4-chlorophenoxy)-1-propanol and 10.5 g of triethylamine in 250 ml of dichloromethane chilled to −5° C. is added dropwise 6.7 g of methanesulfonyl chloride. After chilling and stirring for 1 hour, the mixture is washed with chilled 100 ml portions of water, 10% hydrochloric acid, saturated sodium bicarbonate, and saturated sodium chloride. The organic layer is dried (magnesium sulfate) and the solvent removed under vacuum to give the product as an oil which crystallizes on standing.

EXAMPLE 43

4-2-[4-chlorophenoxy)propyl]amino Benzoic Acid

A mixture of 15 g of crude ethyl 4-2-[4-chlorophenoxy)propyl]amino benzoate, 15 g of potassium hydroxide and 100 ml of 95% ethanol is refluxed for 3 hours. The solution is cooled, diluted with 100 ml of water and 14 ml of conc. hydrochloric acid is added. Chilling gives 1.8 g of solid which is recrystallized from hexane-chloroform to give 1.7 g of product as tan crystals, mp 160°–163° C.

EXAMPLE 44

2,3-Dihydroxypropyl 4-(3-phenoxypropylamino)benzoate

A solution of 5.5 g of 4-(3-phenoxypropylamino)benzoic acid, 4.80 g of 25% aqueous sodium hydroxide, and 12.6 g of 3-iodo-1,2-propanediol in 50 ml of hexamethylphosphoramide is stirred for 24 hours at ambient temperature, diluted with 100 ml of ether and stirred for 5 days at ambient temperature. The mixture is treated with water and extracted with ether. The dried extracts are evaporated to yield 2,3-dihydroxypropyl 4-(3-phenoxypropylamino)benzoate as a white solid.

EXAMPLE 45

2,3-Dihydroxypropyl 4-(3-phenoxypropylamino)benzoate

A solution of 5.5 g. of 4-(3-phenoxypropylamino)benzoic acid in 50 ml. of hexamethylphosphoramide is treated with 4.80 g. of 25% aqueous sodium hydroxide followed by 11.0 g. of 3-chloro-1,2-propanediol and then is heated at 140° C. for 6 hours. The mixture is diluted with water and ether and filtered to yield a white solid. Recrystallization from acetonitrile affords pure 2,3-dihydroxypropyl 4-(3-phenoxypropylamino)benzoate as a white crystalline solid.

EXAMPLE 46

2-p-Fluorophenoxypropionic Acid

To 83 g. of sodium hydride in 100 ml. of dry dimethoxyethane at 5° C. was added a solution of 15.3 g. of 2-bromopropionic acid in 50 ml. of dimethoxyethane and 10.5 g. of 4-fluorophenol in 50 ml. of dimethoxyethane. The slurry was heated to reflux for 6 hours, cooled and filtered. The crude solid was partitioned between methylenechloride and 1 N hydrochloric acid and this process repeated. The organic layer was dried and evaporated to 50 ml. The crystals were collected, washed with hexane and dried, m.p. 113°–115° C.

EXAMPLE 47

2-(p-fluorophenoxy)propanol

To 95 ml. of diborane in 95 ml. of tetrahydrofuran was added 10.2 g. of 2-(4-fluorophenoxy)propionic acid in 100 ml. of tetrahydrofuran. The reaction mixture was stirred at room temperature for 20 hours. The solution was gradually poured onto 600 g. of ice and extracted (3×−250 ml each) with chloroform. The combined organic layer was extracted with water (3×−50 ml each) and dried. The solvent was removed under vacuum giving a clear liquid.

EXAMPLE 48

2-(4-fluorophenoxy)propyl-O-methanesulfonate

To a solution of 7.7 g of 2-(4-fluorophenoxy)propanol and 12.5 ml of triethyl amine in 400 ml of methylene chloride at −5° C. was added 8.8 ml of methane-sulfonyl chloride. After one hour at 0° C. to −8° C., the mixture is washed with cold water, 10% hydrochloric acid, saturated sodium bicarbonate solution, saturated salt solution and dried, giving a light yellow liquid.

EXAMPLE 49

Ethyl p-2-(4-fluorophenoxy)propylaminobenzoate

A solution of 11.98 g of 2-(4-fluorophenoxy)-propyl O-methanesulfonate and 15.2 g of ethyl 4-aminobenzoate in 200 ml. of dry hexamethylphosphoramide was stirred at 120°–130° C. for 46 hours. The solution was diluted with water (200 ml) and extracted with 250 ml of ether (3×). The combined ether layer was extracted with water (3×−100 ml each) and dried. The solution was concentrated and chromatographed on silica gel, and eluted with chloroform. The solution was evaporated and the residue was recrystallized from acetone-water and a second time from ether, yielding a white solid, m.p. 96°–98° C.

EXAMPLE 50 p-2-(4-fluorophenoxy)propylaminobenzoic acid

A solution of 2.6 g of ethyl p-[2-(4-fluorophenoxy)-propylaminobenzoate in 100 ml of 95% ethanol containing 2.7 g of potassium hydroxide was heated to reflux for 2 hours. The reaction was cooled, diluted with 100 ml of water and neutralized with 37% hydrochloric acid. The solid was collected and dried giving a white solid which was dissolved in 25 ml of chloroform and diluted with 1 ml of hexane giving a solid with a m.p. 171°–172° C.

EXAMPLE 51

2-(4-fluorophenoxy)ethanol

To 200 ml of 1 M diborane in tetrahydrofuran was added dropwise 17.0 L g of 4-fluorophenoxyacetic acid in 100 ml of tetrahydrofuran at 5°–10° C. The reaction was stirred at room temperature overnight and poured into a mixture of 100 ml of ice and 750 ml of chloroform. The water phase was extracted twice more with 250 ml each of chloroform and the combined organic phase dried. This solution was concentrated to a light yellow oil. This material was placed on the Kugelrohr (vacuum distillation) giving 14.8 g on distillation.

EXAMPLE 52

2-(4-fluorophenoxy)ethyl O-methanesulfonate

A solution of 125 g of 2-(4-fluorophenoxy)ethanol and 23 ml of triethylamine in 100 ml of methylenechloride at −5° C. was stirred under $N_2$ while 7 ml of methanesulfonyl chloride in 50 ml of methylenechloride was added. The solution was stirred for 2 hours at room temperature and extracted with water, 10% hydrochloric acid, saturated sodium bicarbonate solution and brine. The organic layer was dried and evaporated to a clear liquid used for alkylation in the next example.

EXAMPLE 53

Ethyl p-2-(4-fluorophenoxy)ethylaminobenzoate

A solution of 18 g. of 2-(4-fluorophenoxy)ethyl O-methanesulfonate and 27 g. of ethyl 4-aminobenzoate in 150 ml. of hexamethylphosphoramide was heated 2 days at 120° C. The reaction mixture was then cooled, diluted with 100 ml. of water and the solid collected. The solid was recrystallized from methylenechloride-benzene and was further recrystallized from acetonitrile giving a white solid, m.p. 122°–123° C.

EXAMPLE 54 p-2-(4-fluorophenoxy)ethylaminobenzoic Acid

To ethyl p-2-(4-fluorophenoxy)ethylaminobenzoate was added 6 grams of KOH in 100 ml. of 95% EtOH. The solution was refluxed for three hours and after cooling acidified with 9 ml. of conc. 37% hydrochloric acid. The solution was diluted with 50 ml. of water. The solid was collected and recrystallized from a mixture of acetonitrile and ethyl acetate and was further recrystallized from tetrahydrofuran-hexane giving a white powder, m.p. 209°–210° C.

We claim:

1. The method of treating lipidemia in a mammal which comprises administering orally to a mammal afflicted with lipidemia an effective amount therefor of a compound selected from the group consisting of those of the formula:

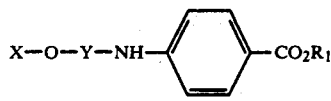

wherein Y is a branched or straight chain alkylene group of the formula $C_nH_{2n}$ wherein n is 2 to 12, $R_1$ is selected from the group consisting of hydrogen, lower alkyl, di(lower alkyl)-aminoethyl, 2,3-dihydroxypropyl, 2-(lower alkanoylamino)ethyl and 1-methyl-4-piperidyl, X is selected from the group consisting of phenyl, naphthyl, thienyl, furyl, 1,2,3,4-tetrahydronaphthyl, 4-chloro-1-naphthyl and substituted phenyl wherein the phenyl substituents are halogen, hydroxy, lower alkoxy, lower alkyl, cyano, trihalomethyl, amino, lower alkanoylamino, lower alkylamino, di(lower alkyl)amino, phenoxy, p-chlorophenoxy, benzyloxy, p-chlorobenzyloxy or cycloalkyl; the pharmacologically acceptable acid-addition salts thereof; and the pharmacologically acceptable cationic salts thereof when $R_1$ is hydrogen.

2. The method according to claim 1 wherein the compound is p-{[2-(1-naphthyloxy)ethyl]amino}benzoic acid.

3. The method according to claim 1 wherein the compound is p-[(3-phenoxypropyl)amino]benzoic acid.

4. The method according to claim 1 wherein the compound is p-[(2-phenoxypropyl)amino]benzoic acid.

5. The method according to claim 1 wherein the compound is p-{[2-(2-naphthyloxy)ethyl]amino}benzoic acid.

6. The method according to claim 1 wherein the compound is p-{[3-(p-chlorophenoxy)propyl]amino}-benzoic acid.

7. The method according to claim 1 wherein the compound is p-{[2-(p-chlorophenoxy)propyl]amino}-benzoic acid.

8. The method according to claim 1 wherein the compound is p-{[2-(p-chlorophenoxy)-2,2-dimethylethyl]amino}-benzoic acid.

9. The method according to claim 1 wherein the compound is p-2-(4-fluorophenoxy)propylamino benzoic acid.

10. The method according to claim 1 wherein the compound is p-2-(4-fluorophenoxy)ethylamino benzoic acid.

* * * * *